(12) United States Patent
Onushko et al.

(10) Patent No.: US 12,082,794 B2
(45) Date of Patent: Sep. 10, 2024

(54) OCCLUSIVE MEDICAL DEVICE WITH SEALING MEMBER

(71) Applicant: BOSTON SCIENTIFIC SCIMED, INC., Maple Grove, MN (US)

(72) Inventors: David John Onushko, Minneapolis, MN (US); Jose A. Meregotte, Blaine, MN (US); Steven R. Larsen, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 357 days.

(21) Appl. No.: 16/136,674

(22) Filed: Sep. 20, 2018

(65) Prior Publication Data

US 2019/0083075 A1 Mar. 21, 2019

Related U.S. Application Data

(60) Provisional application No. 62/560,796, filed on Sep. 20, 2017.

(51) Int. Cl.
*A61B 17/00* (2006.01)
*A61B 17/12* (2006.01)
*A61B 90/00* (2016.01)

(52) U.S. Cl.
CPC .... *A61B 17/0057* (2013.01); *A61B 17/12122* (2013.01); *A61B 17/12172* (2013.01);
(Continued)

(58) Field of Classification Search
CPC .......... A61B 17/0057; A61B 17/12122; A61B 2017/00867; A61B 17/1214; A61B 17/12022; A61B 17/12131; A61B 17/12172; A61B 17/12109; A61B 17/12113; A61B 17/12177; A61B 17/12027; A61B 17/12031; A61B 17/12036; A61B 17/1204; A61B 2017/00575; A61B 2017/00579;
(Continued)

(56) References Cited

U.S. PATENT DOCUMENTS 6,231,561 B1 5/2001 Frazier et al.
7,727,189 B2 6/2010 VanTassel et al.
(Continued)

FOREIGN PATENT DOCUMENTS

CN 1399571 A 2/2003
EP 1595504 A1 11/2005
(Continued)

OTHER PUBLICATIONS

International Search Report and Written Opinion dated Jan. 21, 2019 for International Application No. PCT/US2018/051953.
(Continued)

*Primary Examiner* — Erich G Herbermann
(74) *Attorney, Agent, or Firm* — Seager, Tufte & Wickhem LLP

(57) ABSTRACT

An example occlusive implant is disclosed. The example occlusive implant includes an expandable framework configured to shift between a collapsed configuration and an expanded configuration, an occlusive member disposed along at least a portion of the expandable framework and a sealing member disposed along the occlusive member.

14 Claims, 16 Drawing Sheets

(52) U.S. Cl.
CPC ............... *A61B 17/12177* (2013.01); *A61B 2017/00526* (2013.01); *A61B 2017/00867* (2013.01); *A61B 2017/00893* (2013.01); *A61B 2017/1205* (2013.01); *A61B 17/12109* (2013.01); *A61B 2090/3966* (2016.02)

(58) Field of Classification Search
CPC .......... A61B 2017/00632; A61B 2017/00601; A61B 17/12111; A61B 2090/3966; A61B 2017/00526; A61B 2017/00893; A61B 2017/1205; A61F 2/01; A61F 2002/0016
See application file for complete search history.

(56) References Cited

U.S. PATENT DOCUMENTS

| | | | |
|---|---|---|---|
| 7,972,359 B2 | 7/2011 | Kreidler | |
| 8,221,384 B2 | 7/2012 | Frazier et al. | |
| 8,562,509 B2 | 10/2013 | Bates | |
| 2003/0208214 A1 | 11/2003 | Loshakove et al. | |
| 2004/0220682 A1 | 11/2004 | Levine et al. | |
| 2005/0125020 A1 | 6/2005 | Meade et al. | |
| 2008/0281350 A1* | 11/2008 | Sepetka ........... | A61B 17/12172 606/200 |
| 2009/0005803 A1 | 1/2009 | Batiste | |
| 2009/0254195 A1 | 10/2009 | Khairkhan et al. | |
| 2011/0054515 A1* | 3/2011 | Bridgeman ...... | A61B 17/12122 606/200 |
| 2012/0172654 A1 | 7/2012 | Bates | |
| 2012/0245619 A1 | 9/2012 | Guest et al. | |
| 2012/0323267 A1* | 12/2012 | Ren ................. | A61B 17/12172 606/191 |
| 2013/0006343 A1 | 1/2013 | Kassab et al. | |
| 2013/0178889 A1* | 7/2013 | Miles ................ | A61B 17/0057 606/200 |
| 2014/0188157 A1 | 7/2014 | Clark | |
| 2015/0133989 A1* | 5/2015 | Lubock ............ | A61B 17/12109 606/200 |
| 2015/0196300 A1 | 7/2015 | Tischler et al. | |

FOREIGN PATENT DOCUMENTS

| | | | | |
|---|---|---|---|---|
| EP | 2481381 A1 | 8/2012 | | |
| JP | 2003532457 A | 11/2003 | | |
| JP | 2005324019 A | 11/2005 | | |
| JP | 2007513684 A | 5/2007 | | |
| WO | 0035352 A1 | 6/2000 | | |
| WO | 03032818 A2 | 4/2003 | | |
| WO | 2007044536 A2 | 4/2007 | | |
| WO | 2010024801 A1 | 3/2010 | | |
| WO | WO-2013059743 A1 * | 4/2013 | ........... | A61F 2/2418 |
| WO | 2014106239 A1 | 7/2014 | | |

OTHER PUBLICATIONS

Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.

* cited by examiner

OCCLUSIVE MEDICAL DEVICE WITH SEALING MEMBER

CROSS-REFERENCE TO RELATED APPLICATIONS

This application claims the benefit of priority under 35 U.S.C. § 119 to U.S. Provisional Application Ser. No. 62/560,796, filed Sep. 20, 2017, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

An example occlusive implant includes an expandable framework configured to shift between a collapsed configuration and an expanded configuration, an occlusive member disposed along at least a portion of the expandable framework and a sealing member disposed along the occlusive member.

In addition or alternatively, wherein the sealing member extends radially outward from the occlusive member.

In addition or alternatively, wherein the occlusive member, the sealing member or both the occlusive member and the sealing member are formed from a fabric.

In addition or alternatively, wherein the sealing member extends around only a portion of the outer surface of the occlusive member.

In addition or alternatively, wherein the sealing member extends circumferentially around the outer surface of the occlusive member.

In addition or alternatively, wherein the sealing member forms a folded portion along an outer surface of the occlusive member.

In addition or alternatively, wherein the occlusive member includes a woven fiber and wherein the sealing member is formed from the woven fiber of the occlusive member.

In addition or alternatively, wherein the sealing member includes an expandable element disposed along a portion of the sealing member.

In addition or alternatively, wherein the sealing member includes one or more flaps extending radially away from the occlusive member.

In addition or alternatively, wherein the expandable framework includes a plurality of anchor members extending radially outward from the expandable framework.

In addition or alternatively, wherein the expandable framework and the plurality of anchor members are formed from a unitary tubular member.

In addition or alternatively, wherein the wherein at least a portion of the plurality of anchor members extend through an aperture formed in the occlusive member.

Another example medical implant for occluding a left atrial appendage, comprising: an expandable framework configured to shift between a collapsed configuration and an expanded configuration;

a plurality of anchor members disposed along the expandable framework;

a covering disposed along an outer surface of the expandable framework; and a protrusion portion extending outward from the covering.

In addition or alternatively, wherein the covering is formed from a fabric.

In addition or alternatively, wherein the covering extends along only a portion of the covering of the expandable framework.

In addition or alternatively, wherein the protrusion portion extends circumferentially around an outer surface of the covering.

In addition or alternatively, wherein the protrusion portion forms a fold along an outer surface of the covering.

An example method for occluding a left atrial appendage, the method comprising:

advancing an occlusive implant to the left atrial appendage, the occlusive implant including:
  an expandable framework;
  an occlusive member coupled to the expandable framework; and
  a sealing member coupled to the occlusive member;
expanding the expandable framework within the left atrial appendage;
positioning the sealing member adjacent to the left atrial appendage.

In addition or alternatively, wherein positioning the sealing member adjacent to the left atrial appendage further includes conforming the sealing member to the contour of the left atrial appendage.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
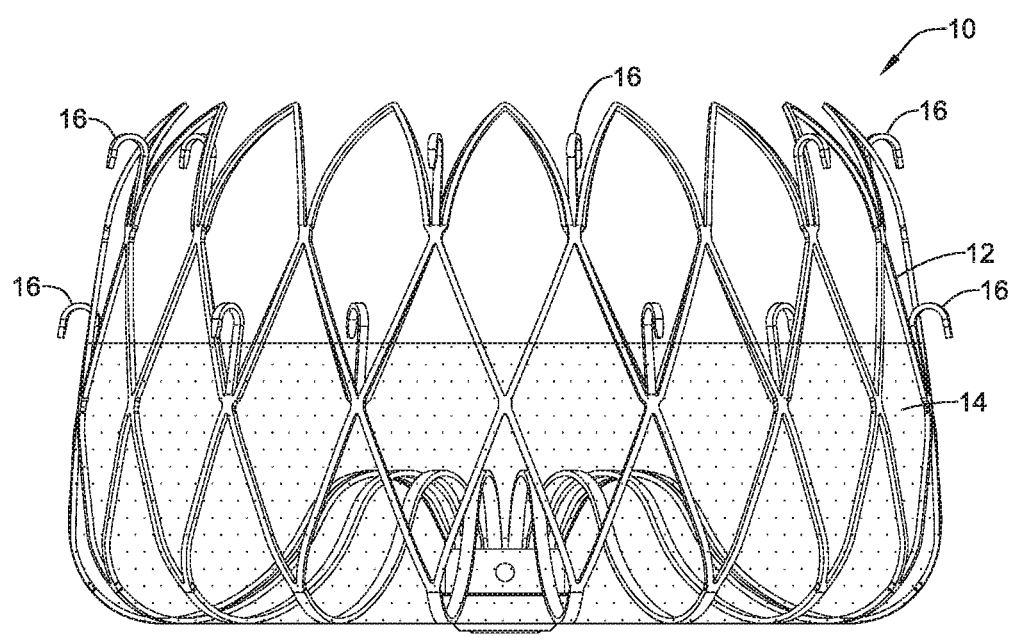
FIG. 1 is a plan view of an example occlusive implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants that close off the left atrial appendage are disclosed herein.

FIG. 1 illustrates an example occlusive implant 10. The implant 10 may include an expandable framework 12. The occlusive implant 10 may also include an occlusive member 14 disposed on, disposed over, disposed about, or covering at least a portion of the expandable framework 12. In some embodiments, the occlusive member 14 may be disposed on, disposed over, disposed about or cover at least a portion of an outer (or outwardly-facing) surface of the expandable framework 12. FIG. 1 further illustrates that the occlusive member 14 may extend only partially along the longitudinal extent of the expandable framework 12. However, this is not intended to be limiting. Rather, the occlusive member 14 may extend along the longitudinal extent of the expandable framework to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a fabric, a polymeric membrane, a metallic or polymeric mesh, a porous filter-like material, or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelization after implantation, thereby effectively removing the left atrial appendage from the patient's circulatory system. Some suitable, but non-limiting, examples of materials for the occlusive member 14 are discussed below.

FIG. 1 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 1. Some suitable, but non-limiting, examples of materials for the expandable framework 12 and/or the plurality of anchor members 16 are discussed below.

In some examples, the expandable framework 12 and the plurality of anchor members 16 may be integrally formed and/or cut from a unitary member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

As illustrated in FIG. 1, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

Figure 2:
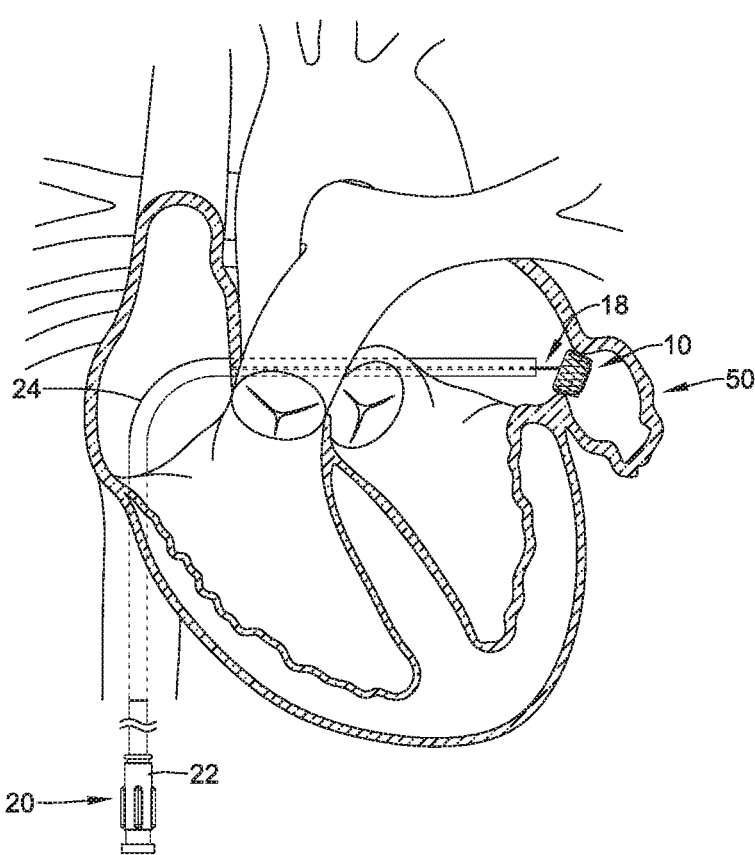
FIG. 2 shows an example occlusive implant positioned in the heart.

FIG. 2 illustrates that the occlusive implant 10 may be inserted and advanced through a body lumen via an occlusive implant delivery system 20. FIG. 2 further illustrates the occlusive implant 10 being delivered and positioned within the left atrial appendage 50. In some instances, an occlusive implant delivery system 20 may include a delivery catheter 24 which is guided toward the left atrium via various chambers and lumens of the heart (e.g., the inferior vena cava, the right atrium, etc.) to a position adjacent the left atrial appendage 50.

The delivery system 20 may include a hub member 22 coupled to a proximal region of the delivery catheter 24. The hub member 22 may be manipulated by a clinician to direct the distal end region of the delivery catheter 24 to a position adjacent the left atrial appendage 50. In some embodiments, an occlusive implant delivery system may include a core wire 18. Further, a proximal end of the expandable framework 12 may be configured to releasably attach, join, couple, engage, or otherwise connect to the distal end of the core wire 18. In some embodiments, an end region of the expandable framework 12 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the expandable framework 12 to the distal end of the core wire 18 are also contemplated.

Figure 3:
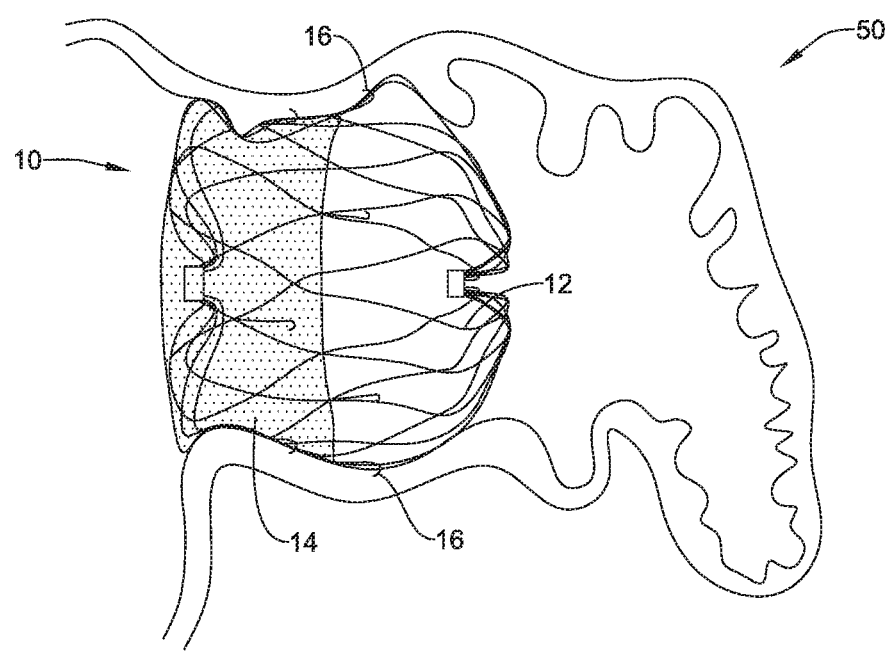
FIG. 3 shows an example occlusive implant positioned in the left atrial appendage.

FIG. 3 illustrates a left atrial appendage occlusive implant 10 positioned adjacent the left atrial appendage 50 via the delivery catheter 24 (described above with respect to FIG. 2). As discussed above, in some examples, the implant 10 may be configured to shift between a collapsed configuration and an expanded configuration. For example, in some instances, the occlusive implant may be in a collapsed configuration during delivery via occlusion implant delivery system, whereby the occlusive implant expands to an expanded configuration once deployed from the occlusion implant delivery system.

Additionally, FIG. 3 illustrates that the expandable framework 12 may be compliant and, therefore, substantially conform to and/or be in sealing engagement with the shape and/or geometry of a lateral wall of a left atrial appendage in the expanded configuration. In some embodiments, the occlusive implant 10 may expand to a size, extent, or shape less than or different from a maximum unconstrained extent, as determined by the surrounding tissue and/or lateral wall of the left atrial appendage. Additionally, FIG. 3 illustrates that the expandable framework 12 may be held fixed adjacent to the left atrial appendage by one or more anchoring members 16.

Further, it can be appreciated that the elements of the expandable framework 12 may be tailored to increase the flexibility and compliance of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant within the left atrial appendage. Several example occlusion devices including various sealing features are disclosed below.

Figure 4:
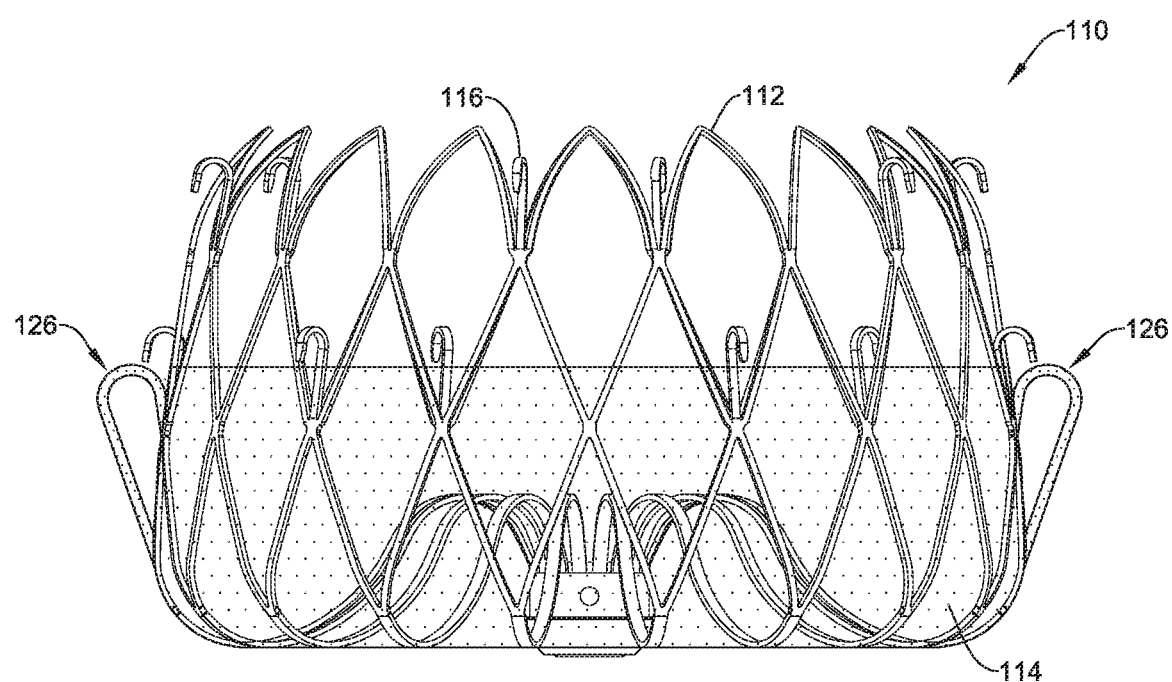
FIG. 4 illustrates an example occlusive implant.

FIG. 4 illustrates an example occlusion implant device 110. The occlusion implant device 110 may be similar in form and function to other occlusion implant devices disclosed herein. For example, the occlusion implant device 110 may include an expandable frame 112, an occlusion member 114 and one or more anchoring members 116. Additionally, FIG. 4 illustrates that the occlusion device 110 may include a sealing member 126. The sealing member 126 may extend outward from the occlusion member 114 and/or the expandable framework 112. For example, the sealing member 126 may extend radially away from the occlusion member 114 and/or the expandable framework 112.

As illustrated in FIG. 4, the sealing member 126 may include a folded portion. It can be appreciated that the folded portion of the sealing member 126 adds "extra" material the occlusion device 110 which, as stated above, extends radially outward from the occlusion member 114 and/or the expandable framework 112. It can be further appreciated that this extra material (defining the sealing member) may be able to conform to the specific shape and/or geometry of a lateral wall of a left atrial appendage. In other words, the sealing member 126 may resemble extra material which may bunch, fill and/or conform to the specific shape and/or geometry of a lateral wall of a left atrial appendage when positioned adjacent thereto.

In some instances, the sealing member 126 may be formed from the same material as the material forming the occlusive member 114. For example, in some instances the sealing member 126 may be formed integral with the occlusive member 114. In other words, the material forming the sealing member 126 may be an extension of the material forming the occlusive member 114. For example, in some instances the occlusive member 114 may be formed from a fabric material, and therefore, in some instances the sealing member may be formed from the same fabric. However, this is not intended to be limiting. Rather, it is contemplated that in some examples the sealing member 126 may be formed from a material which is distinct from the material forming the occlusive member 114. For example, in some instances the sealing member 126 may be formed separate from and later attached (e.g., joined, adhered, sewn, etc.) to the occlusive member 114. Some suitable, but non-limiting, examples of materials for the occlusive members disclosed herein are discussed below.

Additionally, it is contemplated that the sealing member 126 illustrated in FIG. 4 may extend either partially or entirely around the outer surface of the occlusive member 114. For example, the sealing member 126 may extend either partially or entirely around the circumference of the occlusive member 114 and/or expandable framework 112. It can be appreciated that in instances in which the sealing member 126 extends entirely around the outer surface of the occlusive member 112, the sealing member 126 may resemble an annular ring having an open space existing therein. It can be appreciated that the open space permits the sealing member to conform to the specific geometry of the let atrial appendage, thereby permitting the sealing member 126 to sufficiently seal against the lateral wall of the left atrial appendage.

Figure 5:
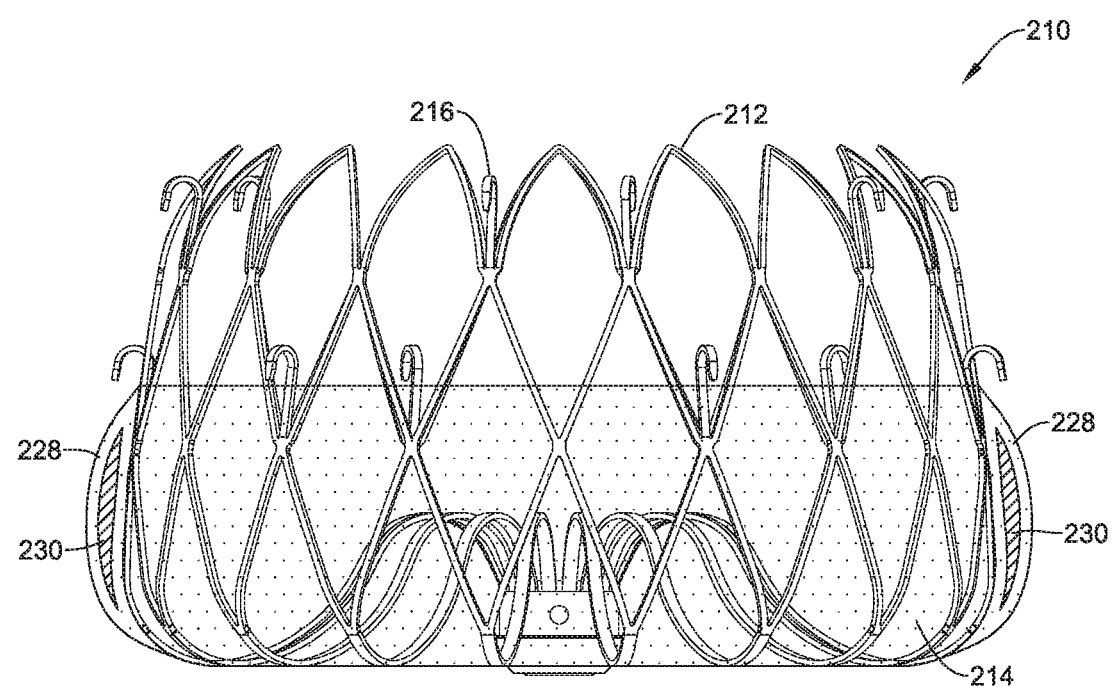
FIG. 5 illustrates another example occlusive implant.

FIG. 5 illustrates another example occlusion implant device 210. The occlusion implant device 210 may be similar in form and function to other occlusion implant devices disclosed herein. For example, the occlusion implant device 210 may include an expandable frame 212, an occlusion member 214 and one or more anchoring members 216. Additionally, FIG. 5 illustrates that the occlusion device 210 may include a sealing member 228.

The sealing member 228 may be similar in form and function to the sealing member 126 described above with respect to FIG. 4. For example, the sealing member 228 may extend outward from the occlusion member 214 and/or the expandable framework 212. Additionally, the sealing member 228 may be formed from the same material as the material forming the occlusive member 214. In other words, the material forming the sealing member 228 may be an extension of the material forming the occlusive member 214. However, this is not intended to be limiting. Rather, it is contemplated that in some examples the sealing member 228 may be formed from a material which is distinct from the material forming the occlusive member 214. Additionally, it is contemplated that the sealing member 228 illustrated in FIG. 5 may extend either partially or entirely around the outer surface of the occlusion member 214 and/or the expandable member 212. For example, the sealing member 228 may extend either partially or entirely around the circumference of the expandable member 212.

FIG. 5 further illustrates that in some examples the occlusion device 210 may include a conformable material 230 which is positioned behind, along or adjacent the sealing member 228 and/or the occlusion member 214. For example, in some instances, the conformable material 230 maybe positioned within a pocket created between the occlusion member 214 and the sealing member 228. The conformable material 230 may include a sheath, mesh, fabric, sheet or similar type material. Further, it can be appreciated that the conformable material 230 illustrated in FIG. 5 may extend either partially or entirely around the outer surface of the occlusion member 214 and/or the expandable member 212. For example, the conformable material 230 may extend either partially or entirely around the circumference of the expandable member 212.

Figure 5A:
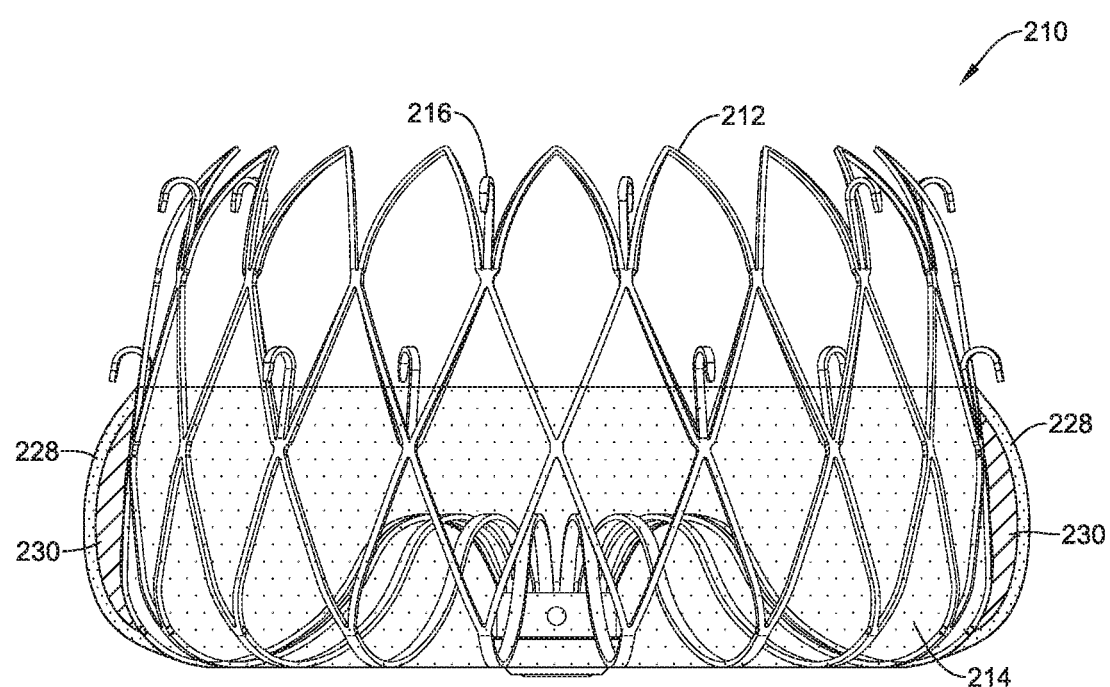
FIG. 5A illustrates another example occlusive implant.

However, in other examples the conformable material 230 may be positioned directly atop the expandable framework 212 and underneath the occlusion member 214 (e.g., between the expandable framework 212 and the occlusion member 214). For example, FIG. 5A illustrates the conformable material 230 positioned directly atop the expandable framework 212 and underneath the occlusion member 214. This configuration may reduce the likelihood of thrombus formation within the occlusion device 210 because the conformable material 230 would be positioned underneath the occlusion member 214 when sealing the left atrial appendage.

In some instances the conformable material 230 described above may be formed from a material which is designed to expand and/or swell upon placement of the occlusion device 210. For example, in some instances the conformable material 230 may be constructed from a hydrogel material. The hydrogel material may swell due to its interaction with water and/or thermal phase changes. However, this is not intended to be limiting. Other materials which may expand or swell are contemplated herein.

Figure 6:
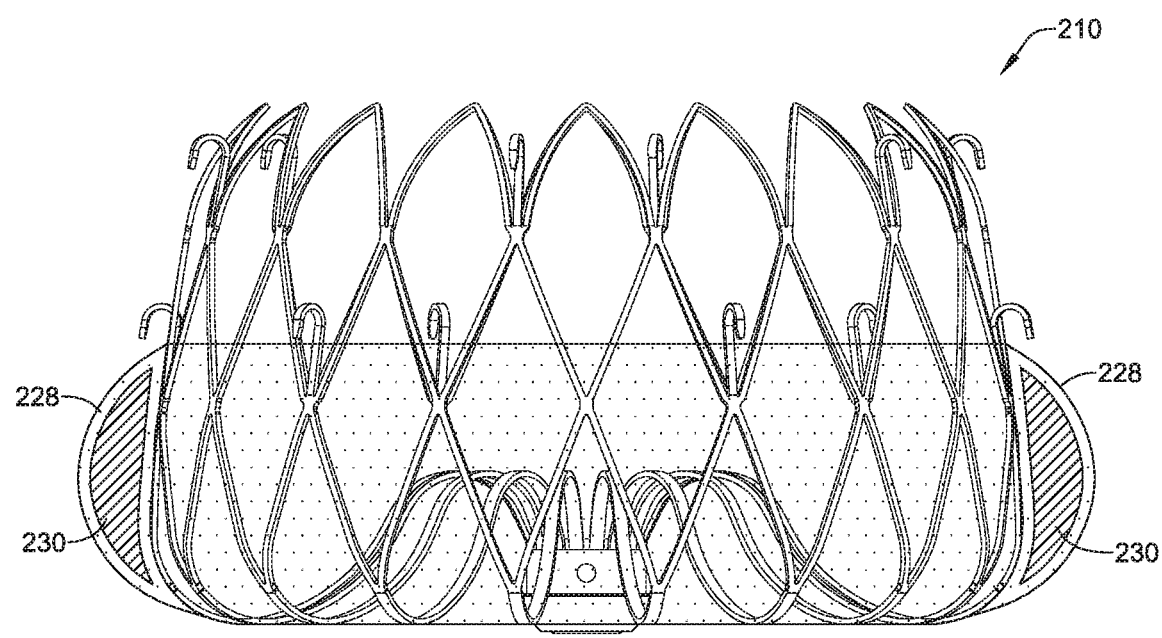
FIG. 6 illustrates another example occlusive implant.

It can be appreciated that designing the conformable material 230 (described with respect to FIG. 5 and FIG. 5A) to include an expandable material may permit the sealing member 228 to effectively seal irregular anatomical geometries of the left atrial appendage. FIG. 6 illustrates the conformable material 230 described with respect to FIG. 5 and FIG. 5A in an expanded state. It can be appreciated that as the conformable material 230 expands (e.g., when adjacent the left atrial appendage), it may conform to the specific geometries of the wall of the left atrial appendage.

Figure 7:
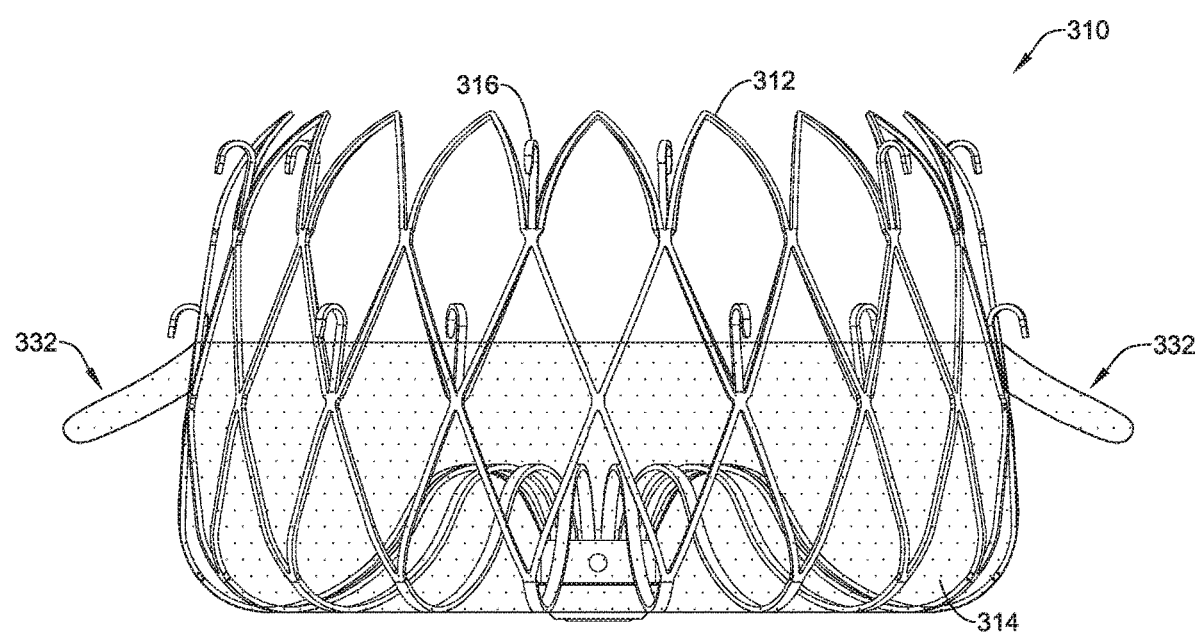
FIG. 7 illustrates another example occlusive implant.

FIG. 7 illustrates another example occlusion implant device 310. The occlusion implant device 310 may be similar in form and function to other occlusion implant devices disclosed herein. For example, the occlusion implant device 310 may include an expandable frame 312, an occlusion member 314 and one or more anchoring members 316.

Figure 8:
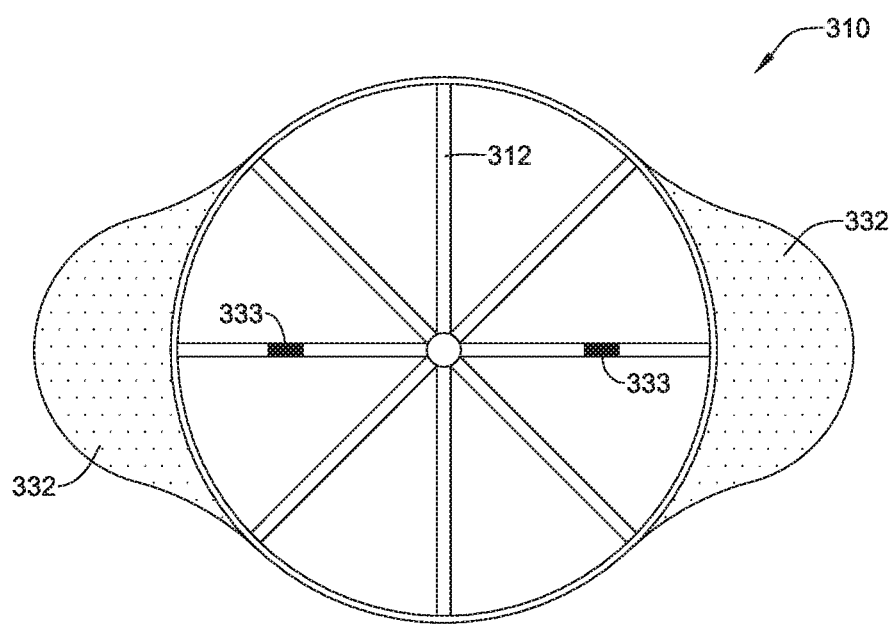
FIG. 8 illustrates a top view of the occlusive implant shown in FIG. 7.

Additionally, FIG. 7 illustrates that the occlusion device 310 may include one or more sealing members 332. Sealing members 332 may extend radially away from the expandable member 312 and/or the occlusion member 314. In some examples the sealing members 332 may resemble "paddles" which extend radially outward from the expandable member 312 and/or the occlusion member 314. For example, FIG. 8 illustrates a top-view of the occlusive device 310 shown in FIG. 7. FIG. 8 shows that the sealing members 332 may include a curved portion which extends radially outward from the expandable framework 312.

Further, while the occlusive device 310 shown in FIG. 8 includes two sealing members 332, this is not intended to be limiting. Rather, it is contemplated that the occlusive device 310 may include 1, 2, 3, 4, or more sealing members 332. Further, the sealing members 332 may be positioned symmetrically around the perimeter of the expandable framework 312. In other instances, however, the sealing members 332 may be positioned asymmetrically around the expendable framework 312. It can be appreciated that the sealing members 332 described above may be designed to seal against the left atrial appendage in a manner similar to other sealing members described herein. For example, the sealing members 332 shown in FIG. 8 may designed to conform to the specific geometries of the wall of the left atrial appendage.

Further, it can be appreciated that in some instances, a clinician may position the occlusive device 310 in a specific orientation within the left atrial appendage to optimize the sealing ability of the occlusive device 310. Therefore, in some instances, it may be desirable to design the occlusive device 310 to permit a clinician to visualize the orientation of the sealing members 332 within the left atrial appendage. For example, FIG. 8 illustrates that in some examples the occlusive device 310 may include one or more radiopaque marker bands 333 which are aligned with each of the sealing members 332, respectively. It can be appreciated that these marker bands may permit a clinician to visual the orientation of the occlusive device 310 within the left atrial appendage. The arrangement of the marker bands 333 shown in FIG. 8 are not limiting, rather, other arrangements and configurations of the marker bands are contemplated.

Figure 9:
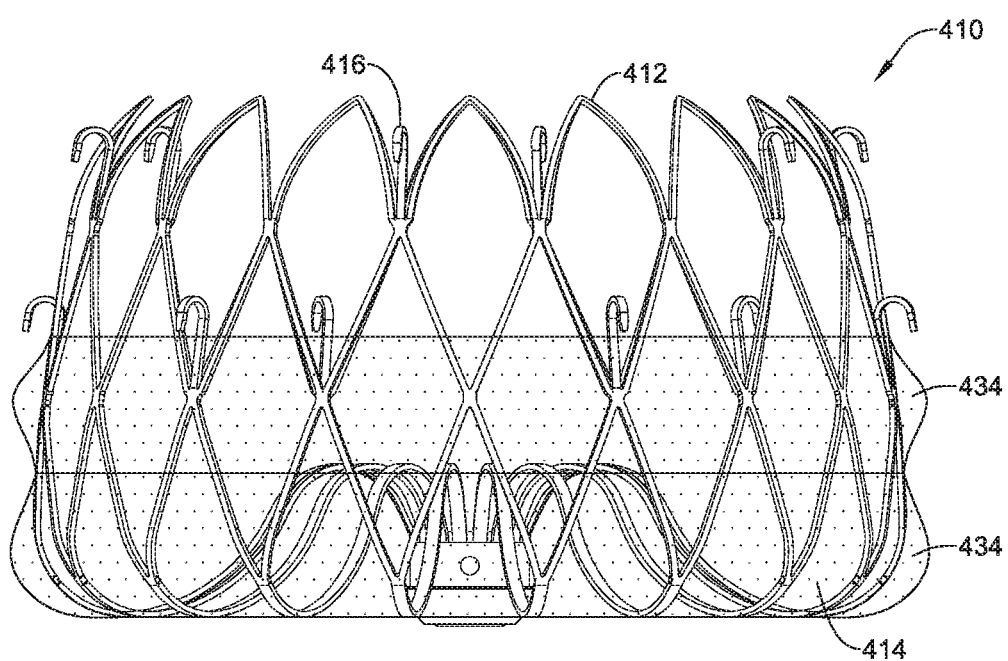
FIG. 9 illustrates another example occlusive implant.

FIG. 9 illustrates another example occlusion implant device 410. The occlusion implant device 410 may be similar in form and function to other occlusion implant devices disclosed herein. For example, the occlusion implant device 410 may include an expandable frame 412, an occlusion member 414 and one or more anchoring members 416.

Additionally, FIG. 9 illustrates that the occlusion device 410 may include one or more sealing members 434. In some examples, the sealing members 434 may be positioned directly adjacent one another. However, in other examples the sealing members 434 may be spaced from one another. Sealing members 434 may extend radially away from the expandable member 412 and/or the occlusion member 414. In some examples the sealing members 434 may resemble "pillows" which extend radially outward from the expandable member 412 and/or the occlusion member 414.

As illustrated in FIG. 9, the sealing members 434 may include "extra" material that extends radially outward from the occlusion member 414 and/or the expandable framework 412. It can be further appreciated that this extra material (defining the sealing members 434) may be able to conform to the specific shape and/or geometry of a lateral wall of a left atrial appendage. In other words, the sealing members 434 may resemble extra material that may bunch, fill and/or conform to the specific shape and/or geometry of a lateral wall of a left atrial appendage when positioned adjacent thereto.

In some instances, the sealing members 434 may be formed from the same material as the material forming the occlusive member 414. In other words, the material forming the sealing members 434 may be an extension of the material forming the occlusive member 414. For example, in some instances the occlusive member 414 may be formed from a fabric material, and therefore, in some instances the sealing member may be formed from the same fabric. However, this is not intended to be limiting. Rather, it is contemplated that in some examples the sealing members 434 may be formed from a material which is distinct from the material forming the occlusive member 414. It is contemplated that the sealing members 434 may be formed from a variety of fibers, bands, sheet material, mesh materials, ring strictures, or the like. These materials may be woven, braided, knitted, or combined using a variety of manufacturing techniques. In some examples the sealing members 434 may extend around the expandable framework in a helical manner.

Additionally, it is contemplated that the sealing members 434 illustrated in FIG. 9 may extend either partially or entirely around the outer surface of the occlusive member 414. For example, the sealing members 434 may extend either partially or entirely around the circumference of the occlusive member 414 and/or expandable framework 412. It can be appreciated that in instances in which the sealing members 434 extend entirely around the outer surface of the occlusive member 414, the sealing members 434 may resemble annular rings extending around the outer surface of the occlusive member 414.

Figure 10:
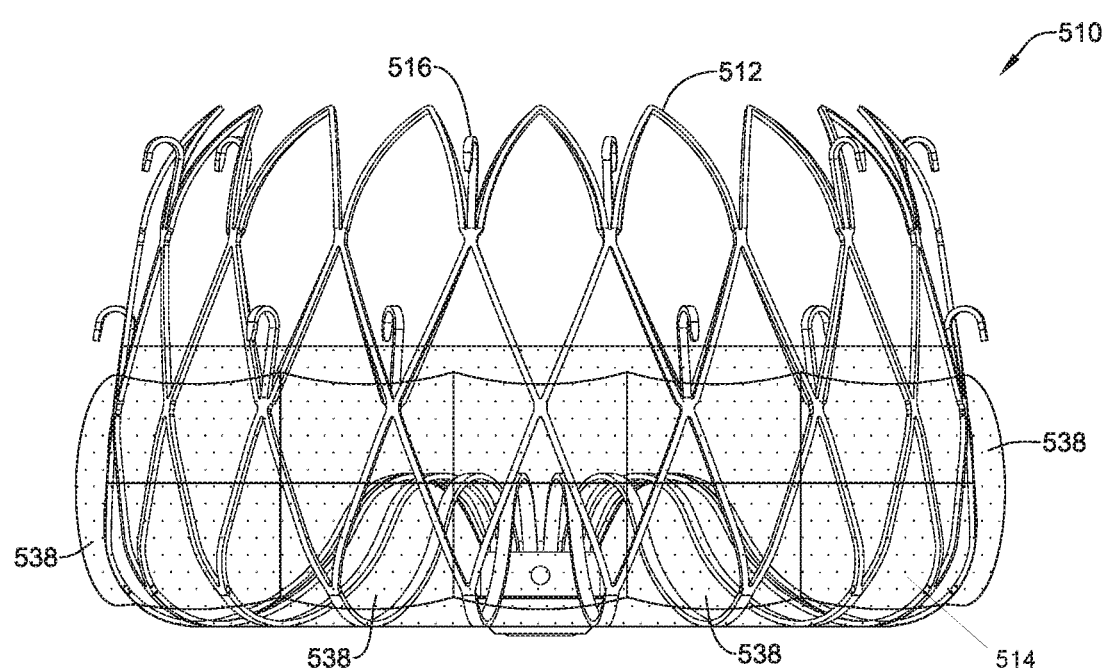
FIG. 10 illustrates another example occlusive implant.

FIG. 10 illustrates another example occlusion implant device 510. The occlusion implant device 510 may be similar in form and function to other occlusion implant devices disclosed herein. For example, the occlusion implant device 510 may include an expandable frame 512, an occlusion member 514 and one or more anchoring members 516.

Additionally, FIG. 10 illustrates that the occlusion device 510 may include one or more sealing members 538. The sealing members 538 may be similar to the sealing members 434 described above with respect to FIG. 9. However, the sealing members 538 may be arranged in "vertical" orientation with respect to the longitudinal axis of the occlusion device 510 (versus being arranged horizontally around the perimeter of the occlusion device 510 as shown in FIG. 9). However, similar to the sealing members 434 described with respect to FIG. 9, the sealing members 538 may extend radially away from the expandable member 512 and/or the occlusion member 514. In some examples the sealing members 538 may resemble vertical "pillows" which extend radially outward from the expandable member 512 and/or the occlusion member 514.

Figure 11:
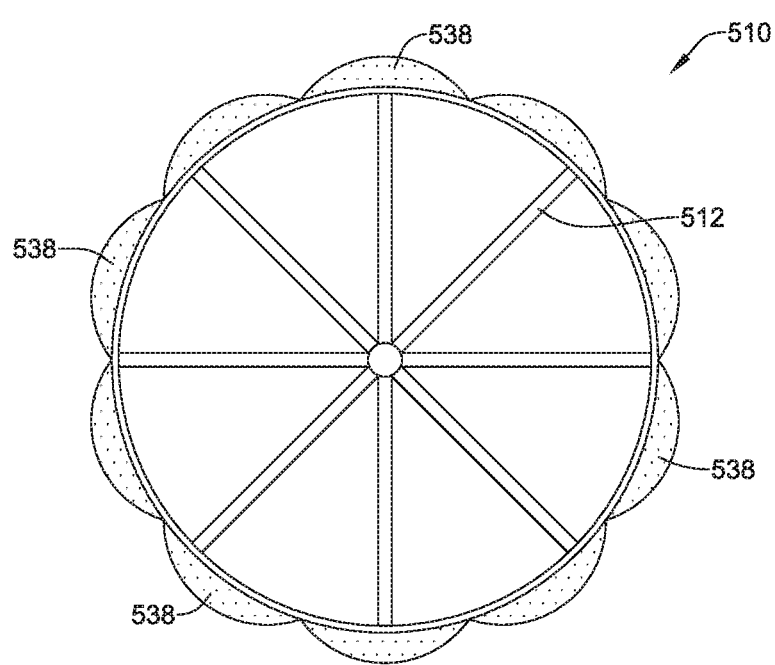
FIG. 11 illustrates a top view of the occlusive implant shown in FIG. 10.

FIG. 11 illustrates a top-view of the occlusive device 510 shown in FIG. 10. In some examples, the sealing members 538 may be positioned directly adjacent one another. However, in other examples the sealing members 538 may be spaced from one another. Additionally, FIG. 11 shows that the sealing members 538 may include a curved portion which extends radially outward from the expandable framework 512. Further, while the occlusive device 510 shown in FIG. 11 includes ten sealing members 538, this is not intended to be limiting. Rather, it is contemplated that the occlusive device 510 may include more or less than ten sealing members 538. For example, the occlusive device 510 may include 1, 2, 3, 4, 5, 6, 7, 8, 9, 10, 11, 12, 13, 14, 15 or more sealing members 538.

Additionally, the sealing members 538 may be positioned symmetrically around the perimeter of the expandable framework 512. In other instances, however, the sealing members 538 may be positioned asymmetrically around the expendable framework 512. It can be appreciated that the sealing members 538 described above may be designed to seal against the left atrial appendage in a manner similar to other sealing members described herein. For example, the sealing members 538 shown in FIG. 10 and FIG. 11 may be designed to conform to the specific geometries of the wall of the left atrial appendage. As illustrated in FIG. 10 and FIG. 11, the sealing members 538 may include "extra" material that extends radially outward from the occlusion member 514 and/or the expandable framework 512. It can be further appreciated that this extra material (defining the sealing members 538) may be able to conform to the specific shape and/or geometry of a lateral wall of a left atrial appendage. Additionally, while not shown in the figures, it is contemplated that the sealing members 538 are configured to lengthen along the vertical axis of the occlusion device 510 in instances in which the occlusion device 510 lengthens along its longitudinal axis.

Figure 12:
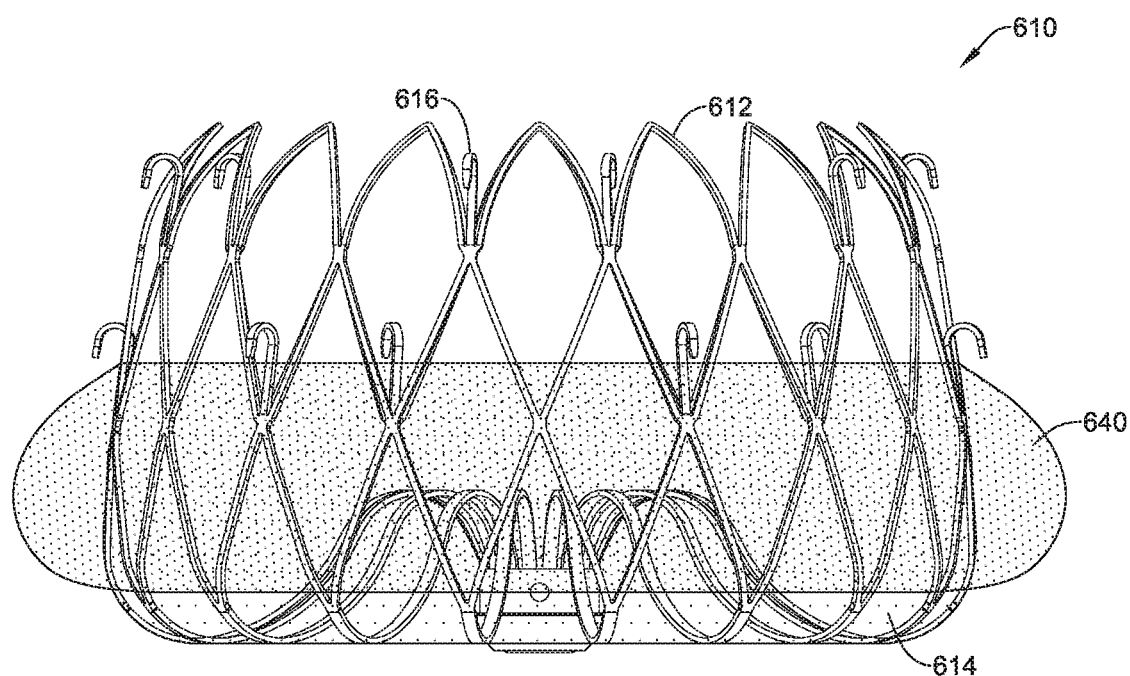
FIG. 12 illustrates another example occlusive implant.

FIG. 12 illustrates another example occlusion implant device 610. The occlusion implant device 610 may be similar in form and function to other occlusion implant devices disclosed herein. For example, the occlusion implant device 610 may include an expandable frame 612, an occlusion member 614 and one or more of the anchoring members 616.

Additionally, FIG. 12 illustrates that the occlusion device 610 may include a sealing member 640. The sealing member 640 may resemble an "annular flap" that extends around the outer surface of the occlusion member 614 and/or the expandable member 612. The sealing member 640 may extend radially away from the expandable member 612 and/or the occlusion member 614. It can be appreciated that the sealing member 640 may provide extra material which is able to conform to the specific shape and/or geometry of a lateral wall of a left atrial appendage. In other words, the sealing member 640 may resemble extra material which may bunch, fill and/or conform to the specific shape and/or geometry of a lateral wall of a left atrial appendage when positioned adjacent thereto.

In some instances, the sealing member 640 may be formed from the same material as the material forming the occlusive member 614. In other words, the material forming the sealing member 640 may be an extension of the material forming the occlusive member 614. For example, in some instances the occlusive member 614 may be formed from a fabric material, and therefore, in some instances the sealing member 640 may be formed from the same fabric. However, this is not intended to be limiting. Rather, it is contemplated that in some examples the sealing member 640 may be formed from a material which is distinct from the material forming the occlusive member 614. Some suitable, but non-limiting, examples of materials for the occlusive members disclosed herein are discussed below.

Additionally, it is contemplated that the sealing member 640 illustrated in FIG. 12 may extend either partially or entirely around the outer surface of the occlusive member 614. For example, the sealing member 640 may extend either partially or entirely around the circumference of the occlusive member 614 and/or expandable framework 612. It can be appreciated that in instances in which the sealing member 640 extends entirely around the outer surface of the occlusive member 612, the sealing member 640 may resemble a flat, annular ring extending entirely around the outer surface of the occlusive member 612.

Figure 13:
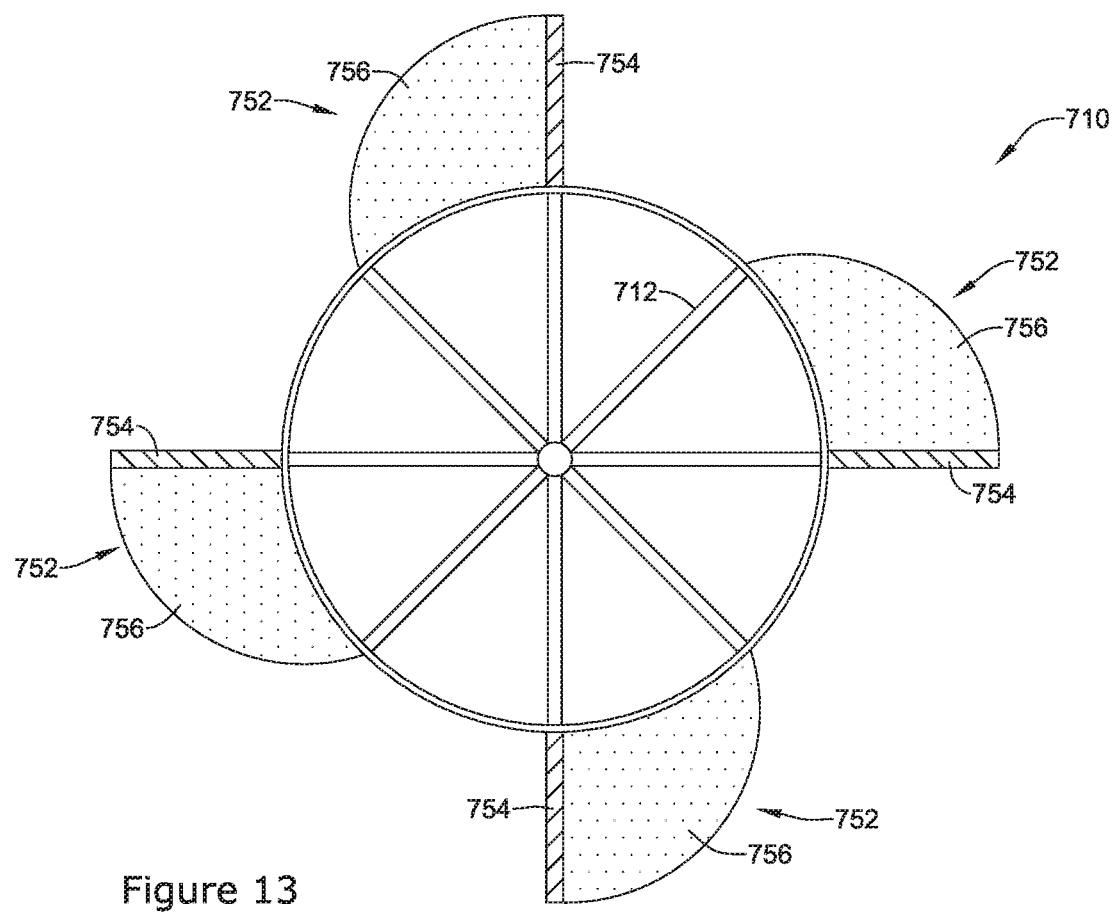
FIG. 13 is a top view of an example occlusive implant.

FIG. 13 illustrates a top view of another example occlusion implant device 710. The occlusion implant device 710 may be similar in form and function to other occlusion implant devices disclosed herein. For example, the occlusion implant device 710 may include an expandable frame 712 and one or more sealing members 752. As illustrated in FIG. 13, sealing members 752 may include a support member 754 which may extend radially away from the expandable frame 712. Additionally, the sealing members 752 may include an occlusion member 756 which may be coupled to both the support member 754 and a portion of the expandable frame 712. The occlusion members 756 may extend along the entire longitudinal length of the expandable frame 712.

Figure 14:
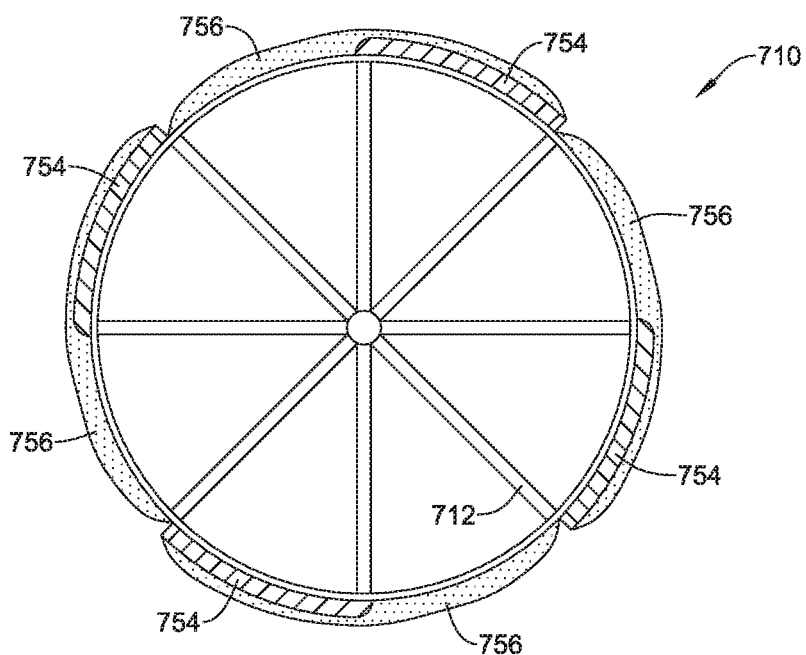
FIG. 14 illustrates the occlusive implant of FIG. 13 in a collapsed configuration.

FIG. 14 illustrates that in some instances, the support arms 754 may bend and/or pivot around the outer circumference of the expandable frame 712. In some instances, the support arms 754 may pivot and collapse around the perimeter of the expandable frame 712 (as shown in FIG. 14), as each of the support arms 754 engage with the lateral wall of the left atrial appendage (for example, as the occlusion implant device is being positioned adjacent the left atrial appendage). It can be appreciated that as each of the support arms 754 pivot and collapse with the lateral wall of the left atrial appendage, the occlusion material 756 that is coupled to the support arms 754 and the expandable frame 712 may seal the occlusive device 710 against the lateral wall of the left atrial appendage.

Figure 15:
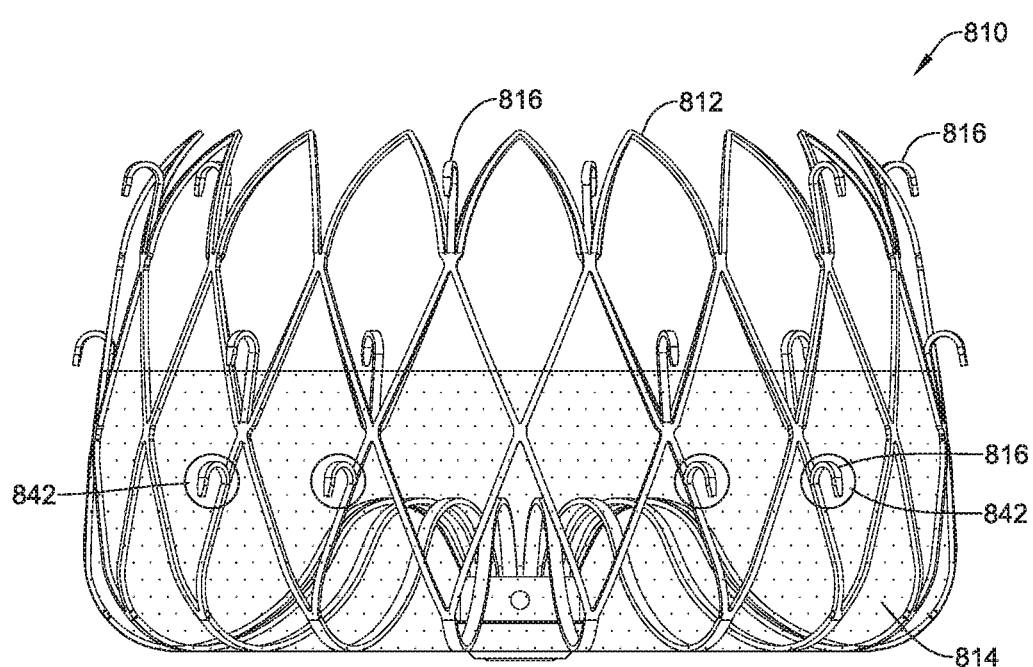
FIG. 15 illustrates another example occlusive implant.

FIG. 15 illustrates another example occlusion implant device 810. The occlusion implant device 810 may be similar in form and function to other occlusion implant devices disclosed herein. For example, the occlusion implant device 810 may include an expandable frame 812, an occlusion member 814 and one or more of the anchoring members 816. Additionally, FIG. 15 illustrates that in some instances the occlusion member 814 may include one or more apertures 842 which permit one or more of the anchoring members 816 to extend therethrough. It can be appreciated that the apertures 842 may be strategically positioned along the occlusion member 814 to align with one or more anchoring members 816. It can be further appreciated that the anchoring members 816 may be arranged along the expandable frame 812 to provide an optimal anchoring of the occlusion implant device 810 within the left atrial appendage. It is contemplated that the apertures 842 described herein may be applied to any of the occlusion implant device configurations described herein.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:
   an expandable framework configured to shift between a collapsed configuration and an expanded configuration, the expandable framework extending from a proximal terminal end of the occlusive implant to a distal terminal end of the occlusive implant, wherein a proximal portion of the expandable framework includes the proximal terminal end and a distal portion of the expandable framework includes the distal terminal end;
   an occlusive member disposed along at least the proximal portion of the expandable framework,
   wherein when deployed in the expanded configuration within a left atrial appendage the occlusive member is configured and adapted to close off the left atrial appendage from a heart and/or a circulatory system; and
   at least two sealing members disposed along the occlusive member, the at least two sealing members in contact with and extending radially outward from the occlusive member, the at least two sealing members including a proximal sealing member and a distal sealing member, where the distal sealing member extends radially outward only as far as or less than the proximal sealing member, wherein the distal portion of the expandable framework is devoid of the sealing member.

2. The occlusive implant of claim 1, wherein the occlusive member, the at least two sealing members or both the occlusive member and the at least two sealing members are formed from a fabric.

3. The occlusive implant of claim 1, wherein the at least two sealing members extends circumferentially around an outer surface of the occlusive member.

4. The occlusive implant of claim 1, wherein the at least two sealing members forms a folded portion along an outer surface of the occlusive member.

5. The occlusive implant of claim 4, wherein the occlusive member includes a woven fiber and wherein the at least two sealing members are formed from the woven fiber of the occlusive member.

6. The occlusive implant of claim 1, wherein the at least two sealing members includes an expandable element disposed along a portion of the at least two sealing members.

7. The occlusive implant of claim 1, wherein the at least two sealing members includes one or more flaps extending radially away from the occlusive member.

8. The occlusive implant of claim 1, wherein the expandable framework includes a plurality of anchor members extending radially outward from the expandable framework.

9. The occlusive implant of claim 8, wherein the expandable framework and the plurality of anchor members are formed from a unitary tubular member.

10. The occlusive implant of claim 1, wherein the occlusive member defines at least part of a proximalmost face of the occlusive implant and a majority of the proximalmost face of the occlusive implant is devoid of the at least two sealing members.

11. A medical implant for occluding a left atrial appendage, comprising:
    an expandable framework configured to shift between a collapsed configuration and an expanded configuration, the expandable framework extending from a proximal terminal end of the medical implant to a distal terminal end of the medical implant, wherein a proximal portion of the expandable framework includes the proximal terminal end and a distal portion of the expandable framework includes the distal terminal end;
    a plurality of anchor members disposed along the expandable framework;
    a covering disposed along an outer surface of the expandable framework, wherein when deployed in the expanded configuration within a left atrial appendage the covering is configured and adapted to close off the left atrial appendage from a heart and/or a circulatory system; and
    a protrusion portion in contact with and extending radially outward from the covering, wherein the protrusion portion extends over only the proximal portion of the expandable framework, the protrusion portion forming an annular ring defining a proximal outermost circumference of the medical implant adjacent the proximal terminal end, wherein the proximal outermost circumference is equal to or larger than an outermost circumference of any other portion of the medical implant when the expandable framework is in the expanded configuration.

12. The medical implant of claim 11, wherein the covering is formed from a fabric.

13. The medical implant of claim 11, wherein the protrusion portion extends circumferentially around an outer surface of the covering.

14. The medical implant of claim 13, wherein the protrusion portion forms a fold along an outer surface of the covering.

* * * * *